US006541014B2

(12) United States Patent
Rudnic et al.

(10) Patent No.: US 6,541,014 B2
(45) Date of Patent: Apr. 1, 2003

(54) ANTIVIRAL PRODUCT, USE AND FORMULATION THEREOF

(75) Inventors: Edward M. Rudnic, N. Potomac, MD (US); James D. Isbister, Potomac, MD (US); Donald J. Treacy, Jr., Arnold, MD (US); Sandra E. Wassink, Frederick, MD (US)

(73) Assignee: Advancis Pharmaceutical Corp., Gaithersburg, MD (US)

( * ) Notice: Subject to any disclaimer, the term of this patent is extended or adjusted under 35 U.S.C. 154(b) by 0 days.

(21) Appl. No.: 09/791,906

(22) Filed: Feb. 22, 2001

(65) Prior Publication Data

US 2002/0068085 A1 Jun. 6, 2002

Related U.S. Application Data

(63) Continuation-in-part of application No. 09/687,237, filed on Oct. 13, 2000.

(51) Int. Cl.[7] .............................. A61K 9/00; A61K 9/48; A61K 9/20; A61K 9/14; A61K 9/16
(52) U.S. Cl. ........................ 424/400; 424/451; 424/464; 424/489; 424/490; 424/492; 424/497; 424/502
(58) Field of Search ................................. 424/451, 457, 424/464, 468, 489, 400, 490, 492, 497, 502

(56) References Cited

U.S. PATENT DOCUMENTS

| | | | |
|---|---|---|---|
| 4,616,008 A | 10/1986 | Hirai et al. .................. 514/200 |
| 4,794,001 A | * 12/1988 | Mehta et al. ................ 424/458 |
| 4,831,025 A | 5/1989 | Godtfredsen et al. ....... 514/195 |
| 4,904,476 A | 2/1990 | Mehta et al. ................ 424/456 |
| 4,915,953 A | 4/1990 | Jordan et al. ................ 424/473 |
| 4,971,805 A | 11/1990 | Kitanishi et al. ............ 424/494 |
| 5,110,597 A | 5/1992 | Wong et al. ................. 424/438 |
| 5,213,808 A | 5/1993 | Bar-Shalom et al. ........ 424/473 |
| 5,229,131 A | 7/1993 | Amidon et al. |
| 5,395,626 A | * 3/1995 | Kotwal et al. ............... 424/472 |
| 5,414,014 A | 5/1995 | Schneider et al. .......... 514/535 |
| 5,445,829 A | 8/1995 | Paradissis et al. .......... 424/480 |
| 5,462,747 A | 10/1995 | Radebaugh et al. ........ 424/465 |
| 5,472,708 A | * 12/1995 | Chen .......................... 424/451 |
| 5,508,040 A | 4/1996 | Chen .......................... 424/451 |
| 5,567,441 A | 10/1996 | Chen .......................... 424/494 |
| 5,672,359 A | 9/1997 | Digenis et al. ............. 424/463 |
| 5,827,531 A | 10/1998 | Morrison et al. ........... 424/450 |
| 5,840,329 A | * 11/1998 | Bai ............................. 424/458 |
| 5,877,243 A | 3/1999 | Sarangapani ................ 524/139 |
| 5,910,322 A | 6/1999 | Rivett et al. |
| 6,027,748 A | 2/2000 | Conte et al. ................ 424/458 |
| 6,132,771 A | 10/2000 | Depui et al. ................ 424/468 |
| 6,294,199 B1 | 9/2001 | Conley et al. .............. 424/468 |
| 6,358,525 B1 | 3/2002 | Guo et al. ................... 424/464 |
| 2001/0046984 A1 | 11/2001 | Rudnic et al. ......... 514/210.09 |
| 2001/0048944 A1 | 12/2001 | Rudnic et al. .............. 424/468 |
| 2002/0004070 A1 | 1/2002 | Rudnic et al. .............. 424/468 |
| 2002/0004499 A1 | 1/2002 | Rudnic et al. .............. 514/192 |

FOREIGN PATENT DOCUMENTS

| | | |
|---|---|---|
| EP | WO 94/27557 | 12/1994 |
| EP | WO 95/20946 | 8/1995 |
| WO | WO 96/04908 | 2/1996 |
| WO | WO 98/22091 | 5/1998 |

* cited by examiner

Primary Examiner—Thurman K. Page
Assistant Examiner—Humera N. Sheikh
(74) Attorney, Agent, or Firm—Elliot M. Olstein; Raymond E. Stauffer

(57) ABSTRACT

An antiviral product is comprised of at least three dosages forms, each of which has a different release profile, with the $C_{max}$ for the antiviral product being reached in less than about twelve hours. In one embodiment, there is an immediate release dosage form, as well as two or more delayed release dosage forms, with each of the dosage forms having a different release profile, wherein each reaches a $C_{max}$ at different times.

32 Claims, No Drawings

ANTIVIRAL PRODUCT, USE AND FORMULATION THEREOF

This application is a continuation-in-part of U.S. application Ser. No. 09/687,237, filed on Oct. 13, 2000.

This invention relates to an antiviral product, as well as the use and formulation thereof.

A wide variety of antivirals have been used, and will be used, in order to combat viral infection. In general, such antivirals can be administered by a repeated dosing of immediate release dosage forms, which results in poor compliance or as a controlled release formulation (slow release) at higher administered doses. The present invention is directed to providing for an improved antiviral product.

In accordance with one aspect of the present invention, there is provided an antiviral pharmaceutical product which is comprised of at least two, preferably at least three, antiviral dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the antiviral contained therein at different times after administration of the antiviral product.

Thus, in accordance with an aspect of the present invention, there is provided a single or unitary antiviral product that has contained therein at least two, preferably at least three antiviral dosage forms, each of which has a different release profile, whereby the antiviral contained in each of such dosage forms is released at different times.

In accordance with a further aspect of the invention, the antiviral product may be comprised of at least four different dosage forms, each of which starts to release the antiviral contained therein at different times after administration of the antiviral product.

The antiviral product generally does not include more than five dosage forms with different release times.

In accordance with a preferred embodiment, the antiviral product has an overall release profile such that when administered the maximum serum concentration of the total antiviral released from the product is reached in less than twelve hours, preferably in less than eleven hours. In an embodiment, the maximum serum concentration of the total antiviral released from the antiviral product is achieved no earlier than four hours after administration.

In accordance with one preferred embodiment of the invention, there are at least three dosage forms. One of the at least three dosage forms is an immediate release dosage form whereby initiation of release of the antiviral therefrom is not substantially delayed after administration of the antiviral product. The second and third of the at least three dosage forms is a delayed dosage form (which may be a pH sensitive or a non-pH sensitive delayed dosage form, depending on the type of antiviral product), whereby the antiviral released therefrom is delayed until after initiation of release of the antiviral from the immediate release dosage form. More particularly, the antiviral release from the second of the at least two dosage forms achieves a $C_{max}$ (maximum serum concentration in the serum) at a time after the antiviral released from the first of the at least three dosage forms achieves a $C_{max}$ in the serum, and the antiviral released from the third dosage form achieves a $C_{max}$ in the serum after the $C_{max}$ of antiviral released from the second dosage form.

In one embodiment, the second of the at least two dosage forms initiates release of the antiviral contained therein at least one hour after the first dosage form, with the initiation of the release therefrom generally occurring no more than six hours after initiation of release of antiviral from the first dosage form of the at least three dosage forms.

In general, the immediate release dosage form produces a $C_{max}$ for the antiviral released therefrom within from about 0.5 to about 2 hours, with the second dosage form of the at least three dosage forms producing a $C_{max}$ for the antiviral released therefrom in no more than about four hours. In general, the $C_{max}$ for such second dosage form is achieved no earlier than two hours after administration of the antiviral product; however, it is possible within the scope of the invention to achieve $C_{max}$ in a shorter period of time.

As hereinabove indicated, the antiviral product may contain at least three or at least four or more different dosage forms. For example, if the antiviral product includes a third dosage form, the antiviral released therefrom reaches a $C_{max}$ at a time later than the $C_{max}$ is achieved for the antiviral released from each of the first and second dosage forms. In a preferred embodiment, release of antiviral from the third dosage form is started after initiation of release of antiviral from both the first dosage form and the second dosage form. In one embodiment, $C_{max}$ for antiviral release from the third dosage form is achieved within eight hours.

In another embodiment, the antiviral product contains at least four dosage forms, with each of the at least four dosage forms having different release profiles, whereby the antiviral release from each of the at least four different dosage forms achieves a $C_{max}$ at a different time.

As hereinabove indicated, in a preferred embodiment, irrespective of whether the antiviral contains at least two or at least three or at least four different dosage forms each with a different release profile, $C_{max}$ for all the antiviral released from the antiviral product is achieved in less than twelve hours, and more generally is achieved in less than eleven hours.

In a preferred embodiment, the antiviral product is a once a day product, whereby after administration of the antiviral product, no further product is administered during the day; i.e., the preferred regimen is that the product is administered only once over a twenty-four hour period. Thus, in accordance with the present invention, there is a single administration of an antiviral product with the antiviral being released in a manner such that overall antiviral release is effected with different release profiles in a manner such that the overall $C_{max}$ for the antiviral product is reached in less than twelve hours. The term single administration means that the total antiviral administered over a twenty-four hour period is administered at the same time, which can be a single tablet or capsule or two or more thereof, provided that they are administered at essentially the same time.

Applicant has found that a single dosage antiviral product comprised of at least three antiviral dosage forms each having a different release profile is an improvement over a single dosage antiviral product comprised of an antiviral dosage form having a single release profile. Each of the dosage forms of antiviral in a pharmaceutically acceptable carrier may have one or more antivirals and each of the dosage forms may have the same antiviral or different antivirals.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antiviral may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antiviral release from such fourth dosage form may be initiated prior to or after release from the second or third dosage form.

The antiviral product of the present invention, as hereinabove described, may be formulated for administration by a variety of routes of administration. For example, the antiviral product may be formulated in a way that is suitable for topical administration; administration in the eye or the ear; rectal or vaginal administration; as nose drops; by inhalation; as an injectable; or for oral administration. In a preferred embodiment, the antiviral product is formulated in a manner such that it is suitable for oral administration.

For example, in formulating the antiviral product for topical administration, such as by application to the skin, the at least two different dosage forms, each of which contains an antiviral, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an antiviral product in the form of a patch, which includes antiviral dosage forms having different release profiles, as hereinabove described.

In addition, the antiviral product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antiviral product with at least three different dosage forms with different release profiles may be formulated for rectal or vaginal administration, as known in the art. This may take the form of a cream or emulsion, or other dissolvable dosage form similar to those used for topical administration.

As a further embodiment, the antiviral product may be formulated for use in inhalation therapy by coating the particles and micronizing the particles for inhalation.

In a preferred embodiment, the antiviral product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antiviral product. Thus, for example, antiviral products may include a first dosage form in the form of a tablet that is an immediate release tablet, and may also include two or more additional tablets, each of which provides for a delayed release of the antiviral, as hereinabove described, whereby the $C_{max}$ of the antiviral released from each of the tablets is reached at different times, with the $C_{max}$ of the total antiviral released from the antiviral product being achieved in less than twelve hours.

The formulation of an antiviral product including at least three dosage forms with different release profiles for different routes of administration is deemed to be within the skill of the art from the teachings herein. As known in the art, with respect to delayed release, the time of release can be controlled by the concentration of antivirals in the coating and/or the thickness of the coating.

In formulating an antiviral product in accordance with the invention, in one embodiment, the immediate release dosage form of the product generally provides from about 20% to about 50% of the total dosage of antiviral to be delivered by the product, with such immediate release dosage forms generally providing at least 25% of the total dosage of the antiviral to be delivered by the product. In many cases, the immediate release dosage form provides from about 20% to about 30% of the total dosage of antiviral to be delivered by the product; however, in some cases it may be desirable to have the immediate release dosage form provide for about 45% to about 50% of the total dosage of antiviral to be delivered by the product.

The remaining dosage forms deliver the remainder of the antiviral. If more than one delayed release dosage form is used, in one embodiment, each of the delayed release dosage forms may provide about equal amounts of antiviral; however, they may also be formulated so as to provide different amounts.

In accordance with the present invention, each of the dosage forms contains the same antiviral; however, each of the dosage forms may contain more than one antiviral.

In one embodiment, where the composition contains one immediate release component and two delayed release components, the immediate release component provides from 20% to 35% (preferably 20% to 30%), by weight, of the total antiviral; where there is three delayed release components, the immediate release component provides from 15% to 30%, by weight, of the total antiviral; and where there are four delayed release components, the immediate release component provides from 10% to 25%, by weight, of the total antiviral.

With respect to the delayed release components, where there are two delayed release components, the first delayed release component (the one released earlier in time) provides from 30% to 60%, by weight, of the total antiviral provided by the two delayed release components with the second delayed release component providing the remainder of the antiviral.

Where there are three delayed release components, the earliest released component provides 20% to 35% by weight of the total antiviral provided by the three delayed release components, the next in time delayed release component provides from 20% to 40%, by weight, of the antiviral provided by the three delayed release components and the last in time providing the remainder of the antiviral provided by the three delayed release components.

When there are four delayed release components, the earliest delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total antiviral provided by the four delayed release components.

The Immediate Release Component

The immediate release portion of this system can be a mixture of ingredients that breaks down quickly after administration to release the antiviral. This can take the form of either a discrete pellet or granule that is mixed in with, or compressed with, the other three components.

The materials to be added to the antivirals for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05–15% (W/W).

The Non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5–25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4–20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose, hydroxypropylmethylcellulose, hydroxypropylcellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4–20% (W/W).

As hereinabove indicated, the units comprising the antiviral composition of the present invention can be in the form of discrete pellets or particles contained in the capsule, or particles embedded in a tablet or suspended in a liquid suspension.

The antiviral composition of the present invention may be administered, for example, by any of the following routes of administration: sublingual, transmucosal, transdermal, parenteral, etc., and preferably is administered orally. The composition includes a therapeutically effective amount of the antiviral, which amount will vary with the antiviral to be used, the disease or infection to be treated, and the number of times that the composition is to be delivered in a day. The composition is administered to a host in an amount effective for treating a viral infection.

The following are representative examples of some antivirals that may be used in the product of the invention: Acyclovir, Amantadine, Amprenavir, Cidofovir, Delavirdine, Didanosine, Famciclovir, Foscarnet, Ganciclovir, Indinavir, Interferon, Lamivudine, Nelfinavir, Nevirapine, Palivizumab, Penciclovir, Ribavirin, Rimantadine, Ritonavir, Saquinavir, Stavudine, Trifluridine, Valacyclovir, Vidarabine, Zalcitabine, Zidovudine.

The invention will be further described with respect to the following examples; however, the scope of the invention is not limited thereby. All percentages in this specification, unless otherwise specified, are by weight.

ANTIVIRAL EXAMPLES

Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum over or forced-air oven. The product may be sieved or granulated, and compressed using a suitable tablet press, such as a rotary table press.

| Ingredient | Conc. (% W/W) |
|---|---|
| Example 1: | |
| Acyclovir | 65% (W/W) |
| Microcrystalline cellulose | 20 |
| Povidone | 10 |
| Croscarmellose sodium | 5 |
| Example 2: | |
| Acyclovir | 55% (W/W) |
| Microcrystalline cellulose | 25 |
| Povidone | 10 |
| Croscarmellose sodium | 10 |
| Example 3: | |
| Acyclovir | 65% (W/W) |
| Microcrystalline cellulose | 20 |
| Hydroxypropylcellulose | 10 |
| Croscarmellose sodium | 5 |
| Example 4: | |
| Acyclovir | 75% (W/W) |
| Polyethylene glycol 4000 | 10 |
| Polyethylene glycol 2000 | 10 |
| Hydroxypropylcellulose | 5 |

| Ingredient | Conc. (% W/W) |
|---|---|
| Example 5: | |
| Acyclovir | 75% (W/W) |
| Polyethylene glycol 8000 | 20 |
| Polyvinylpyrrolidone | 5 |
| Example 6: | |
| Zidovudine | 65% (W/W) |
| Microcrystalline cellulose | 20 |
| Hydroxypropylcellulose | 10 |
| Croscarmellose sodium | 5 |
| Example 7: | |
| Zidovudine | 75% (W/W) |
| Microcrystalline cellulose | 15 |
| Hydroxypropylcellulose | 5 |
| Croscarmellose sodium | 5 |
| Example 8: | |
| Zidovudine | 75% (W/W) |
| Polyethylene glycol 4000 | 10 |
| Polyethylene glycol 2000 | 10 |
| Hydroxypropylcellulose | 5 |
| Example 9: | |
| Zidovudine | 75% (W/W) |
| Polyethylene glycol 8000 | 20 |
| Polyvinylpyrrolidone | 5 |
| Example 10: | |
| Valacyclovir | 65% (W/W) |
| Microcrystalline cellulose | 20 |
| Hydroxypropylcellulose | 10 |
| Croscarmellose sodium | 5 |
| Example 11: | |
| Valacyclovir | 75% (W/W) |
| Microcrystalline cellulose | 15 |
| Hydroxypropylcellulose | 5 |
| Croscarmellose sodium | 5 |
| Example 12: | |
| Valacyclovir | 75% (W/W) |
| Polyethylene glycol 4000 | 10 |
| Polytheylene glycol 2000 | 10 |
| Hydroxypropylcellulose | 5 |
| Example 13: | |
| Cirpofloxacin | 75% (W/W) |
| Polyethylene glycol 8000 | 20 |
| Polyvinylpyrrolidone | 5 |
| Example 14: | |
| Ribavirin | 75% (W/W) |
| Polyethylene glycol 4000 | 10 |
| Polyethylene glycol 2000 | 10 |
| Hydroxypropylcellulose | 5 |
| Example 15: | |
| Ribavirin | 75% (W/W) |
| Polyethylene Glycol 4000 | 20 |
| Polyvinylpyrrolidone | 5 |
| Example 16: | |
| Acyclovir | 65% (W/W) |
| Microcrystalline cellulose | 20 |
| Polyox | 10 |
| Croscarmellose sodium | 5 |
| Example 17: | |
| Acyclovir | 55% (W/W) |
| Microcrystalline cellulose | 25 |
| Polyox | 10 |
| Glyceryl monooleate | 10 |
| Example 18: | |
| Acyclovir | 65% (W/W) |
| Polyox | 20 |
| Hydroxypropylcellulose | 10 |
| Croscarmellose sodium | 5 |
| Example 19: | |
| Acyclovir | 75% (W/W) |
| Polyethylene glycol 4000 | 10 |
| Polyethylene glycol 2000 | 10 |
| Eudragit RL 30D | 5 |
| Example 20: | |
| Acyclovir | 75% (W/W) |
| Polyethylene glycol 8000 | 20 |
| Ethylcellulose | 5 |
| Example 21: | |
| Zidovudine | 70% (W/W) |
| Polyox | 20 |
| Hydroxypropylcellulose | 5 |
| Croscarmellose sodium | 5 |
| Example 22: | |
| Zidovudine | 75% (W/W) |
| Polyox | 15 |
| Hydroxypropylcellulose | 5 |
| Ethylcellulose | 5 |
| Example 23: | |
| Zidovudine | 75% (W/W) |
| Polyethylene glycol 4000 | 10 |
| Polyethylene glycol 2000 | 10 |
| Eudragit RL 30D | 5 |
| Example 24: | |
| Zidovudine | 80% (W/W) |
| Polyethylene glycol 8000 | 10 |
| Polyvinylpyrrolidone | 5 |
| Eudgragit R 30D | 5 |
| Example 25: | |
| Valacyclovir | 65% (WIW) |
| Polyethylene glycol 4000 | 20 |
| Hydroxypropylcellulose | 10 |
| Eudragit RL 30D | 5 |
| Example 26: | |
| Valacyclovir | 75% (W/W) |
| Microcrystalline cellulose | 15 |
| Hydroxypropylcellulose | 5 |
| Ethylcellulose | 5 |
| Example 27: | |
| Valacyclovir | 80% (W/W) |
| Polyethylene glycol 4000 | 10 |
| Polyethylene glycol 2000 | 5 |
| Eudgragit RL 30D | 5 |
| Example 28: | |
| Valacyclovir | 75% (W/W) |
| Polyethylene glycol 8000 | 20 |
| Ethylcellulose | 5 |

Non pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| Ingredient | Conc. (% W/W) |
|---|---|
| Example 29: | |
| Ribavirin | 75% (W/W) |
| Polyethylene glycol 4000 | 10 |
| Polyethylene glycol 2000 | 10 |
| Eudragit RL 30D | 5 |
| Example 30: | |
| Ribavirin | 75% (W/W) |
| Polyethylene glycol 8000 | 20 |
| Ethylcellulose | 5 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| Ingredient | Conc. (% W/W) |
|---|---|
| Example 31: | |
| Acyclovir | 65% (W/W) |
| Microcrystalline cellulose | 20 |
| Cellulose Acetate Pthalate | 15 |
| Example 32: | |
| Acyclovir | 55% (W/W) |
| Microcrystalline cellulose | 25 |
| Cellulose Acetate Pthalate | 10 |
| Hydroxypropylmethylcellulose | 10 |
| Example 33: | |
| Acyclovir | 65% (W/W) |
| Polyox | 20 |
| Hydroxypropylcellulose pthalate | 10 |
| Eudragit L30D | 5 |
| Example 34: | |
| Acyclovir | 75% (W/W) |
| Polyethylene glycol 2000 | 10 |
| Eudragit L 30D | 10 |
| Eudragit RL 30D | 5 |
| Example 35: | |
| Acyclovir | 40% (W/W) |
| Microcrystalline Cellulose | 40 |
| Cellulose Acetate Pthalate | 10 |
| Example 36: | |
| Zidovudine | 70% (W/W) |
| Hydroxypropylcellulose pthalate | 15 |
| Croscarmellose sodium | 10 |
| Example 37: | |
| Zidovudine | 70% (W/W) |
| Eudragit L 30D | 15 |
| Hydroxypropylcellulose | 10 |
| Ethylcellulose | 5 |
| Example 38: | |
| Zidovudine | 75% (W/W) |
| Polyethylene glycol 2000 | 10 |
| Eudragit L 30 D | 15 |

| Ingredient | Conc. (% W/W) |
|---|---|
| Example 39: | |
| Zidovudine | 40% (W/W) |
| Lactose | 50 |
| Eudgragit L 30D | 10 |
| Example 40: | |
| Valacyclovir | 65% (W/W) |
| Microcrystalline Cellulose | 20 |
| Eudragit L 30D | 10 |
| Example 41: | |
| Valacyclovir | 75% (W/W) |
| Microcrystalline Cellulose | 15 |
| Hydroxypropylcellulose pthalate | 10 |
| Example 42: | |
| Valacyclovir | 80% (W/W) |
| Lactose | 10 |
| Eudragit L 30D | 10 |
| Example 43: | |
| Valacyclovir | 70% (W/W) |
| Polyethylene glycol 4000 | 20 |
| Cellulose acetate pthalate | 10 |
| Example 44: | |
| Ribavirin | 60% (W/W) |
| Polyethylene glycol 2000 | 10 |
| Lactose | 20 |
| Eudragit L 30D | 10 |
| Example 45: | |
| Ribavirin | 70% (W/W) |
| Microcrystalline cellulose | 20 |
| Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| Ingredient | Conc. (% W/W) |
|---|---|
| Example 46: | |
| Acyclovir | 65% (W/W) |
| Ethylcellulose | 20 |
| Polyox | 10 |
| Hydroxypropylmethylcellulose | 5 |
| Example 47: | |
| Acyclovir | 55% (W/W) |
| Lactose | 25 |
| Polyox | 10 |
| Glyceryl monooleate | 10 |
| Example 48: | |
| Acyclovir | 70% (W/W) |
| Polyox | 20 |
| Hydroxypropylcellulose | 10 |
| Example 49: | |
| Zidovudine | 75% (W/W) |
| Lactose | 15 |
| Hydroxypropylcellulose | 5 |
| Ethylcellulose | 5 |

-continued

| Ingredient | Conc. (% W/W) |
|---|---|
| Example 50: | |
| Zidovudine | 75% (W/W) |
| Polyethylene glycol 4000 | 10 |
| Lactose | 10 |
| Eudragit RL 30D | 5 |
| Example 51: | |
| Zidovudine | 80% (W/W) |
| Polyethylene glycol 8000 | 10 |
| Hydroxypropylmethylcellulose | 5 |
| Eudgragit RS 30D | 5 |
| Example 52: | |
| Valacyclovir | 75% (W/W) |
| Hydroxyethylcellulose | 10 |
| Polyethylene glycol 4000 | 10 |
| Hydroxypropylcellulose | 5 |
| Example 53: | |
| Valacyclovir | 75% (W/W) |
| Lactose | 10 |
| Povidone (PVP) | 10 |
| Polyethylene glycol 2000 | 5 |
| Example 54: | |
| Ribavirin | 75% (W/W) |
| Polyethylene glycol 4000 | 10 |
| Povidone (PVP) | 10 |
| Hydroxypropylcellulose | 5 |
| Example 55: | |
| Ribavirin | 75% (W/W) |
| Lactose | 15 |
| Polyethylene glycol 4000 | 5 |
| Polyvinylpyrrolidone | 5 |
| Example 56: | |
| Zidovudine | 40% (W/W) |
| Eudragit S100 | 50 |
| Triethyl Citrate | 10 |
| Example 57: | |
| Zidovudine | 50% (W/W) |
| Sureteric | 50 |
| Example 58: | |
| Zidovudine | 50% (W/W) |
| Eudragit S100 | 45 |
| Triethyl Citrate | 5 |

Three Pulses

Example 59

1. Antiviral Matrix Pellet Formulation and Preparation Procedure (Immediate Release)

A. Pellet Formulation

The composition of the antiviral matrix pellets provided in Table 1.

TABLE 1

| Composition of Antiviral Pellets | |
|---|---|
| Component | Percentage (%) |
| Antiviral | 50 |
| Avicel PH 101 | 20 |
| Lactose | 20 |
| PVP K29/32* | |
| Purified Water | 10 |
| Total | 100 |

*PVP K29132 was added as a 20% w/w aqueous solution during wet massing.

B. Preparation Procedure for Antiviral Matrix Pellets 1.2.1 Blend antiviral and Avicel® PH 101 using a Robot Coupe high shear granulator.

1.2.2 Add 20% Povidone K29/32 binder solution slowly into the powder blend under continuous mixing.

1.2.3 Extrude the wet mass using an LCI Bench Top Granulator. The diameter of the screen of the Bench Top Granulator was 1.0 mm.

1.2.4 Spheronize the extrudate using a Model SPH20 Caleva Spheronizer.

1.2.5 Dry the spheronized pellets at 50° C. overnight.

1.2.6 Pellets between 16 and 30 Mesh were collected for further processing.

1.3 Preparation of an Eudragit® L 30 D-55 Aqueous Coating Dispersion

A. Dispersion Formulation

The composition of the aqueous Eudragit L30D-55 dispersion applied to the antiviral matrix pellets is provided below in Table 2.

TABLE 2

| Eudragit ® L 30 D-55 Aqueous Coating Dispersion | |
|---|---|
| Component | Percentage (%) |
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

B. Preparation Procedure for an Eudragit® L 30 D-55 Aqueous Dispersion 1.3.1 Suspend triethyl citrate and talc in deionized water.

1.3.2 The TEC/talc suspension is then homogenized using a PowerGen 700 high shear mixer.

1.3.3 Add the TEC/talc suspension slowly to the Eudragit® L 30 D-55 latex dispersion while stirring.

1.3.4 Allow the coating dispersion to stir for one hour prior to application onto the antiviral matrix pellets.

1.4 Preparation of an Eudragit® S 100 Aqueous Coating Dispersion

A. Dispersion Formulation

The composition of the aqueous Eudragit® S 100 dispersion applied to the antiviral matrix pellets is provided below in Table 3.

TABLE 3

| Eudragit ® S 100 Aqueous Coating Dispersion | |
|---|---|
| Component | Percentage (%) |
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

B. Preparation Procedure for an Eudragit® S 100 Aqueous Dispersion

Part I:

(i) Dispense Eudragit® S 100 powder in deionized water with stirring.

(ii) Add ammonium hydroxide solution drop-wise into the dispersion with stirring.
(iii) Allow the partially neutralized dispersion to stir for 60 minutes.
(iv) Add triethyl citrate drop-wise into the dispersion with stirring. Stir for about 2 hours prior to the addition of Part B.

Part II:
(i) Disperse talc in the required amount of water
(ii) Homogenize the dispersion using a PowerGen 700D high shear mixer.
(iii) Part B is then added slowly to the polymer dispersion in Part A with a mild stirring.

1.5 Coating Conditions for the Application of Aqueous Coating Dispersions

The following coating parameters are used to coat matrix pellets with each of the Eudragit® L 30 D-55 and Eudragit® S 100 aqueous film coating.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
(ii) Coat matrix pellets with S100 dispersion such that you apply 20% coat weight gain to the pellets.

1.6 Encapsulation of the Antiviral Pellets

Pellets are filled into size 00 hard gelatin capsules at a ratio of 30%:30%:40%: Immediate-release matrix pellets uncoated, L30 D-55 coated pellets and S100 coated pellets respectively.

The capsule is filled with the three different pellets to achieve the desired dosage.

Three Pulses

Example 60

Antiviral Pellet Formulation and Preparation Procedure 60.1 Pellet Formulations for Subsequent Coating The composition of the Antiviral trihydrate matrix pellets provided in Table 4.

TABLE 4

Composition of Antiviral Matrix Pellets

| Component | Percentage (%) |
|---|---|
| Antiviral Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

60.2 Preparation Procedure for Antiviral Matrix Pellets 60.2.1 Blend Antiviral and Avicel® PH 101 using a low shear blender.

60.2.2 Add the hydroxypropyl methylcellulose binder solution slowly into the powder blend under continuous mixing.

60.2.3 Extrude the wet mass using an LCI Bench Top Granulator. The diameter of the screen of the Bench Top Granulator is 0.8 mm.

60.2.4 Spheronize the extrudate using a QJ-230 Spheronizer using a small cross section plate.

60.2.5 Dry the spheronized pellets at 60° C. using a fluid bed dryer until the exhaust temperature reaches 40° C.

60.2.6 Pellets between 20 and 40 Mesh were collected for further processing.

60.3 Preparation of an Eudragit® L 30 D-55 Aqueous Coating Dispersion 60.3.1 Dispersion Formulation The composition of the aqueous Eudragit L30D-55 dispersion applied to the antiviral matrix pellets is provided below in Table 5.

TABLE 5

Eudragit ® L 30 D-55 Aqueous Coating Dispersion

| Component | Percentage (%) |
|---|---|
| Eudragit ® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

60.4 Preparation Procedure for an Eudragit® L 30 D-55 Aqueous Dispersion 60.4.1 Suspend triethyl citrate and talc in deionized water.

60.4.2 The TEC/talc suspension is mixed using laboratory mixer.

60.4.3 Add the TEC/talc suspension from slowly to the Eudragit® L 30 D-55 latex dispersion while stirring.

60.4.4 Allow the coating dispersion to stir for one hour prior to application onto the antiviral matrix pellets.

60.5 Preparation of an Eudragit® S 100 Aqueous Coating Dispersion 60.5.1 Dispersion Formulation The composition of the aqueous Eudragit® S 100 dispersion applied to the Antiviral matrix pellets is provided below in Table 6.

TABLE 6

Eudragit ® S 100 Aqueous Coating Dispersion

| Component | Percentage (%) |
|---|---|
| Part A | |
| Eudragit ® S 100 | 10.0 |
| 1 N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

60.6 Preparation Procedure for an Eudragit® S 100 Aqueous Dispersion

Part A:

60.6.1 Dispense Eudragit® S 100 powder in deionized water with stirring.

60.6.2 Add ammonium hydroxide solution drop-wise into the dispersion with stirring.

60.6.3 Allow the partially neutralized dispersion to stir for 60 minutes.

60.6.4 Add triethyl citrate drop-wise into the dispersion with stirring and let stir overnight prior to the addition of Part B.

Part B:

60.6.5 Disperse talc in the required amount of water 60.6.6 Stir the dispersion using an overhead laboratory mixer.

60.6.7 Part B is then added slowly to the polymer dispersion in Part A with a mild stirring.

60.7 Coating Conditions for the Application of Aqueous Coating Dispersions

The following coating parameters are used for both the Eudragit® L 30 D-55 and Eudragit® S 100 aqueous film coating processes.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2–6 gram per minute |

60.7.1 Coat matrix pellets with L30 D-55 dispersion such that you apply 20% coat weight gain to the pellets.

60.7.2 Coat matrix pellets with S100 dispersion such that you apply 37% coat weight gain to the pellets.

60.8 Preparation of Antiviral Granulation (Immediate Release Component) for tabletting

TABLE 7

Composition of Antiviral Granulation

| Component | Percentage (%) |
|---|---|
| Antiviral Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

60.8.1 Blend Antiviral and Avicel® PH 101 using a low shear blender.

60.8.2 Add the hydroxypropyl methylcellulose binder solution slowly into the powder blend under continuous mixing.

60.8.3 Dry the granulation at 60° C. using a fluid bed dryer until the exhaust temperature reaches 40° C.

60.8.4 Granules between 20 and 40 Mesh are collected for further processing.

60.9 Tabletting of the Antiviral Pellets

TABLE 8

Composition of Antiviral Tablets

| Component | Percentage (%) |
|---|---|
| Antiviral granules | 32.5 |
| Avicel PH 200 | 5.0 |
| Antiviral L30D-55 coated pellets | 30 |
| Antiviral S100 coated pellets | 30 |
| Colloidal silicon dioxide | 1.5 |
| Magnesium stearate | 1.0 |
| Total | 100 |

60.9.1 Blend the Antiviral granules, Avicel PH-200, Antiviral pellets and colloidal silicon dioxide for 15 minutes in a tumble blender.

60.9.2 Add the magnesium stearate to the blender, and blend for 5 minutes.

60.9.3 Compress the blend on a rotary tablet press.

60.9.4 The fill weight should be adjusted to achieve the desired dosage.

Four Pulses

Example 61

1 Antiviral Matrix Pellet Formulation and Preparation Procedure 61.1 Pellet Formulation The composition of the antiviral matrix pellets provided in Table 9.

TABLE 9

Composition of Antiviral Pellets

| Component | Percentage (%) |
|---|---|
| Antiviral | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

61.2 Preparation Procedure for Antiviral Matrix Pellets 61.2.1 Blend antiviral and Avicel® PH 101 using a Robot Coupe high shear granulator.

61.2.2 Add 20% Povidone K29/32 binder solution slowly into the powder blend under continuous mixing.

61.2.3 Extrude the wet mass using an LCI Bench Top Granulator. The diameter of the screen of the Bench Top Granulator was 1.0 mm.

61.2.4 Spheronize the extrudate using a Model SPH20 Caleva Spheronizer.

61.2.5 Dry the spheronized pellets at 50° C. overnight.

61.2.6 Pellets between 16 and 30 Mesh were collected for further processing.

61.3 Preparation of an Eudragit® L 30 D-55 Aqueous Coating Dispersion 61.3.1 Dispersion Formulation The composition of the aqueous Eudragit L30D-55 dispersion applied to the antiviral matrix pellets is provided below in Table 10.

TABLE 10

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

61.4 Preparation Procedure for an Eudragit® L 30 D-55 Aqueous Dispersion 61.4.1 Suspend triethyl citrate and talc in deionized water.

61.4.2 The TEC/talc suspension is then homogenized using a PowerGen 700 high shear mixer.

61.4.3 Add the TEC/talc suspension slowly to the Eudragit® L 30 D-55 latex dispersion while stirring.

61.4.4 Allow the coating dispersion to stir for one hour prior to application onto the antiviral matrix pellets.

61.5 Preparation of an Eudragit® S 100 Aqueous Coating Dispersion 61.5.1 Dispersion Formulation The composition of the aqueous Eudragit® S 100 dispersion applied to the antiviral matrix pellets is provided below in Table 11.

TABLE 11

Eudragit ® S 100 Aqueous Coating Dispersion

| Component | Percentage (%) |
|---|---|
| Part A | |
| Eudragit ® S 100 | 12.0 |
| 1 N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

61.6 Preparation Procedure for an Eudragit® S 100 Aqueous Dispersion

Part A:

61.6.1 Dispense Eudragit® S 100 powder in deionized water with stirring.

61.6.2 Add ammonium hydroxide solution drop-wise into the dispersion with stirring.

61.6.3 Allow the partially neutralized dispersion to stir for 60 minutes.

61.6.4 Add triethyl citrate drop-wise into the dispersion with stirring. Stir for about 2 hours prior to the addition of Part B.

Part B:

61.6.5 Disperse talc in the required amount of water 61.6.6 Homogenize the dispersion using a PowerGen 700D high shear mixer.

61.6.7 Part B is then added slowly to the polymer dispersion in Part A with a mild stirring.

61.7 Coating Conditions for the Application of Aqueous Coating Dispersions

The following coating parameters are used for coating with each of the Eudragit® L 30 D-55 and Eudragit® S 100 aqueous film coatings.

| Coating Equipment | STREA 1 ™ Table Top Laboratory Fluid Bed Coater |
|---|---|
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

61.7.1 Coat matrix pellets with L30 D-55 dispersion such that you apply 12% coat weight gain to the pellets.

61.7.2 Coat matrix pellets with L30 D-55 dispersion such that you apply 30% coat weight gain to the pellets.

61.7.3 Coat matrix pellets with S100 dispersion such that you apply 20% coat weight gain to the pellets.

61.8 Encapsulation of the Antiviral Pellets

Pellets are filled into size 00 hard gelatin capsules at a ratio of 20%:30%:20%:30% Immediate-release matrix pellets (uncoated), L30 D-55 coated pellets 12% weight gain, L30D-55 coated pellets 30% weight gain and S100 coated pellets respectively. The capsule is filled with the four different pellets to achieve the desired dosage.

The present invention is particularly advantageous in that there is provided an antiviral product which provides an improvement over twice a day administration of the antiviral and an improvement over a once a day administration of the antiviral.

Numerous modification and variations of the present invention are possible in light of the above teachings and therefore, within the scope of the appended claims the invention may be practiced otherwise than as particularly described.

What is claimed is:

1. A once-a-day antiviral product comprising: first, second, and third antiviral dosage forms, each of said antiviral dosage forms comprising at least one antiviral and a pharmaceutically acceptable carrier, said first antiviral dosage form being an immediate release dosage form, said second and third antiviral dosage forms being delayed release dosage forms, and wherein each of said first, second, and third antiviral dosage forms initiates release of said at least one antiviral at different times, said once-a-day antiviral product further comprising a therapeutically effective amount of said at least one antiviral, said therapeutically effective amount being the total dosage of said at least one antiviral for a twenty-four hour period, and wherein said at least one antiviral released by said once-a-day antiviral product achieves Cmax in serum in less than twelve hours after administration.

2. The product of claim 1, wherein the Cmax for the product is reached no earlier than four hours after administration.

3. The product of claim 1, wherein the antiviral released from the first dosage form reaches a Cmax in serum within from about 0.5 hours to about 2 hours after administration of the product.

4. The product of claim 1, wherein the antiviral released from the second dosage form reaches a Cmax in serum in no more than about 4 hours after administration of the product.

5. The product of claim 1, wherein the antiviral released from the third dosage form reaches a Cmax in serum within 8 hours after administration of the product.

6. The product of claim 1, wherein the immediate release dosage form contains at least 20% and no more than 50% of the total dosage of antiviral.

7. The product of claim 1, wherein the product is an oral dosage form.

8. The product of claim 7, wherein the antiviral released from the second dosage form reaches a Cmax in the serum after Cmax is reached in the serum for the antiviral released from the first dosage form.

9. The product of claim 8, wherein the antiviral released from the third dosage form reaches a Cmax in the serum after Cmax is reached in the serum for the antiviral released from the second dosage form.

10. The product of claim 9, wherein said second dosage form initiates release of said antiviral before said third dosage form, wherein said second dosage form provides from 30% to 60% by weight of the total antiviral released by said second and third dosage forms, and wherein said third dosage form provides the remainder of the total antiviral released by said second and third dosage forms.

11. The product of claim 1 further comprising a fourth antiviral dosage form, said fourth antiviral dosage form comprising at least one antiviral and a pharmaceutically acceptable carrier and wherein said at least one antiviral released from said fourth antiviral dosage form reaches a Cmax in the serum after Cmax is acheived in the serum for antiviral released from each of said first, second, and third dosage forms.

12. The product of claim 11, wherein said fourth antiviral dosage form is a delayed release dosage form.

13. The product of claim 12, wherein said second dosage form initiates release of said antiviral before said third dosage form, wherein said third dosage form initiates release of said antiviral before said fourth dosage form, wherein said second dosage form provides 20% to 35% by weight of the total antiviral released by said second, third, and fourth dosage forms, wherein said third dosage form provides from 20% to 40% by weight of the total antiviral released by said second, third, and fourth dosage forms, and wherein said fourth dosage form provides the remainder of the total antiviral released by said second, third, and fourth dosage forms.

14. The product of claim 11, wherein the antiviral released from the first dosage form reaches a Cmax in serum within from about 0.5 hours to about 2 hours after administration of the product.

15. The product of claim 11, wherein the antiviral released from the second dosage form reaches a Cmax in serum in no more than about 4 hours after administration of the product.

16. The product of claim 11, wherein the antiviral released from the third dosage form reaches a Cmax in serum within 8 hours after administration of the product.

17. A process for treating a viral infection in a host comprising: administering to a host the antiviral product of claim 1 once-a-day.

18. A process for treating a viral infection in a host comprising: administering to a host the antiviral product of claim 2 once-a-day.

19. A process for treating a viral infection in a host comprising: administering to a host the antiviral product of claim 3 once-a-day.

20. A process for treating a viral infection in a host comprising: administering to a host the antiviral product of claim 4 once-a-day.

21. A process for treating a viral infection in a host comprising: administering to a host the antiviral product of claim 5 once-a-day.

22. A process for treating a viral infection in a host comprising: administering to a host the antiviral product of claim 6 once-a-day.

23. A process for treating a viral infection in a host comprising: administering to a host the antiviral product of claim 7 once-a-day.

24. A process for treating viral infection in a host comprising: administering to a host the antiviral product of claim 8 once-a-day.

25. A process for treating a viral infection in a host comprising: administering to a host the antiviral product of claim 9 once-a-day.

26. A process for treating a viral infection in a host comprising: administering to a host the antiviral product of claim 10 once-a-day.

27. A process for treating a viral infection in a host comprising: administering to a host the antiviral product of claim 11 once-a-day.

28. A process for treating a viral infection in a host comprising: administering to a host the antiviral product of claim 12 once-a-day.

29. A process for treating a viral infection in a host comprising: administering to a host the antiviral product of claim 13 once-a-day.

30. A process for treating a viral infection in a host comprising: administering to a host the antiviral product of claim 14 once-a-day.

31. A process for treating a viral infection in a host comprising: administering to a host the antiviral product of claim 15 once-a-day.

32. A process for treating a viral infection in a host comprising: administering to a host the antiviral product of claim 16 once-a-day.

* * * * *

UNITED STATES PATENT AND TRADEMARK OFFICE
CERTIFICATE OF CORRECTION

PATENT NO. : 6,541,014 B2  Page 1 of 3
DATED : April 1, 20003
INVENTOR(S) : Rudnic et al.

It is certified that error appears in the above-identified patent and that said Letters Patent is hereby corrected as shown below:

Column 8,
Lines 20 to 28, delete:

"Example 19:

| | |
|---|---|
| Acyclovir | 75% (W/W) |
| Polyethylene glycol 4000 | 10 |
| Polyethylene glycol 2000 | 10 |
| Eudragit RL 30D | 5 |

Example 20:

| | |
|---|---|
| Acyclovir | 75% (W/W) |
| Polyethylene glycol 8000 | 20 |
| Ethylcellulose | 5 " |

Lines 34 to 66, delete:

"Example 22:

| | |
|---|---|
| Zidovudine | 75% (W/W) |
| Polyox | 15 |
| Hydroxypropylcellulose | 5 |
| Ethylcellulose | 5 |

Example 23:

| | |
|---|---|
| Zidovudine | 75% (W/W) |
| Polyethylene glycol 4000 | 10 |
| Polyethylene glycol 2000 | 10 |
| Eudragit RL 30D | 5 |

Example 24:

| | |
|---|---|
| Zidovudine | 80% (W/W) |

UNITED STATES PATENT AND TRADEMARK OFFICE
CERTIFICATE OF CORRECTION

PATENT NO. : 6,541,014 B2
DATED : April 1, 20003
INVENTOR(S) : Rudnic et al.

It is certified that error appears in the above-identified patent and that said Letters Patent is hereby corrected as shown below:

Column 8 (cont'd),

| | |
|---|---|
| Polyethylene glycol 8000 | 10 |
| Polyvinylpryrrolidine | 5 |
| Eudragit R 30D | 5 |

Example 25:

| | |
|---|---|
| Valacyclovir | 65% (W/W) |
| Polyethlene glycol 4000 | 20 |
| Hydroxypropylcellulose | 10 |
| Eudragit RL 30D | 5 |

Example 26:

| | |
|---|---|
| Valacyclovir | 75% (W/W) |
| Microcrystalline cellulose | 15 |
| Hydroxypropylcellulose | 5 |
| Ethylcellulose | 5 |

Example 27:

| | |
|---|---|
| Valacyclovir | 80% (W/W) |
| Polyethylene glycol 4000 | 10 |
| Polyethylene glycol 2000 | 5 |
| Eudgragit RL 30D | 5 |

Example 28:

| | |
|---|---|
| Valacyclovir | 75% (W/W) |
| Polyethylene glycol 8000 | 20 |
| Ethylcellulose | 5 " |

Column 9,
Lines 5 to 13, delete:

"Example 29:

| | |
|---|---|
| Ribavirin | 75% (W/W) |
| Polyethylene glycol 4000 | 10 |
| Polyethylene glycol 2000 | 10 |
| Eudragit RL 30D | 5 |

Example 30:

| | |
|---|---|
| Ribavirin | 75% (W/W) |
| Polyethylene glycol 8000 | 20 |
| Ethylcellulose | 5 " |

UNITED STATES PATENT AND TRADEMARK OFFICE
CERTIFICATE OF CORRECTION

PATENT NO. : 6,541,014 B2
DATED : April 1, 20003
INVENTOR(S) : Rudnic et al.

It is certified that error appears in the above-identified patent and that said Letters Patent is hereby corrected as shown below:

<u>Column 9 (cont'd),</u>
Lines 45 to 49, delete:

"Example 34:

| Acyclovir | 75% (W/W) |
|---|---|
| Polyethylene glycol 2000 | 10 |
| Eudragit L 30D | 10 |
| Eudragit RL 30D | 5 " |

Lines 58 to 62, delete:

"Example 37:

| Zidovudine | 70% (W/W) |
|---|---|
| Eudragit L 30D | 15 |
| Hydroxypropylcellulose | 10 |
| Ethylcellulose | 5 " |

Signed and Sealed this

Eighth Day of June, 2004

JON W. DUDAS
*Acting Director of the United States Patent and Trademark Office*